United States Patent [19]

Mercuri

[11] 4,161,174
[45] Jul. 17, 1979

[54] BIOMEDICAL ELECTRODE ASSEMBLY

[76] Inventor: Albert R. Mercuri, 502 South Ave., Weston, Mass. 02193

[21] Appl. No.: 922,723

[22] Filed: Jul. 7, 1978

Related U.S. Application Data

[63] Continuation-in-part of Ser. No. 815,180, Jul. 13, 1977, abandoned.

[51] Int. Cl.² ............................................. A61B 5/04
[52] U.S. Cl. .................. 128/641; 339/220 R
[58] Field of Search ............ 128/2.06 E, 2.1 E, 404, 128/410, 411, 416–418, DIG. 4; 339/220 R, 220 C, 220 L, 220 T

[56] References Cited

U.S. PATENT DOCUMENTS

| 3,498,291 | 3/1970 | Bunn | 128/2.06 E |
|---|---|---|---|
| 3,610,229 | 10/1971 | Zenkich | 128/2.06 E |
| 3,805,769 | 4/1974 | Sessions | 128/2.06 E |
| 3,828,766 | 8/1974 | Krasnow | 128/2.1 E |
| 3,845,757 | 11/1974 | Weyer | 128/2.06 E |
| 3,848,600 | 11/1974 | Patrick, Jr. et al. | 128/417 X |
| 3,901,218 | 8/1975 | Buchalter | 128/2.06 E |
| 3,911,906 | 10/1975 | Reinhold, Jr. | 128/2.06 E |

FOREIGN PATENT DOCUMENTS

| 605304 | 9/1960 | Canada | 339/220 R |
|---|---|---|---|
| 123770 | 5/1920 | United Kingdom | 339/220 R |

*Primary Examiner*—Lee S. Cohen
*Attorney, Agent, or Firm*—Joseph S. Iandiorio

[57] ABSTRACT

An electrode assembly for use in a biomedical electrode unit having a contact pad with a hole in it for receiving the electrode assembly including: a first member disposed on one side of the pad and having a stud portion extending axially through the hole in the pad and having a first mating area; a second member disposed on the other side of the pad and having an aperture with a second mating area for snugly engaging the first mating area of the stud portion; and a connector member extending axially through the hole in the pad and into the first and second members for securely connecting together the first and second members with the pad between them.

7 Claims, 6 Drawing Figures

BIOMEDICAL ELECTRODE ASSEMBLY

RELATED CASE

This application is a Continuation-In-Part of U.S. Patent Application Ser. No. 815,180, filed July 13, 1977, entitled BIOMEDICAL ELECTRODE ASSEMBLY by Albert R. Mercuri, now abandoned.

FIELD OF INVENTION

This invention relates to an improved electrode assembly for a biomedical electrode unit.

BACKGROUND OF INVENTION

Electrode assemblies for biomedical electrode units use snap fasteners commonly used on clothing or variations of such fasteners, which are relatively complex, expensive, and difficult to assemble. Since they are made as clothing fasteners they are not ideally suited for use as electrodes. When these and other fasteners are mounted on the adhesive pad which adheres to the skin, the lower and upper electrodes may either squeeze the pad too much and distort it or grip it too loosely so that the electrode can wobble relative to the pad and is not held tightly in contact with the skin. In addition, the upper and lower parts of some fasteners may not always seat tightly together; they can wiggle relative to each other and the pad between them. This instability can result in poor or intermittent contact and result in poor electrical continuity between the upper and lower electrodes. In many constructions the base electrode, which carries a sponge disc impregnated with conductive gel for electrical interface with the skin, is hollow so that the gel can move through it to the junction of the electrodes where it can interfere with and cause corrosion of the parts.

SUMMARY OF INVENTION

It is therefore an object of this invention to provide an improved, inexpensive electrode assembly for a biomedical electrode unit which is simple in construction and easy to assemble.

It is a further object of this invention to provide an electrode assembly which is extremely stable, firmly but gently grips the pad without squashing it, maintains positive electrical interconnection through the electrode assembly, and prevents tilting of the electrode assembly parts relative to each other and the pad.

The invention results from the realization that a truly simple, inexpensive, and easy to assemble electrode assembly can be made using first and second members secured together by a connector member, to obtain mechanically stable, positive electrical coupling and firm gripping of the pad and which can be enhanced by the use of tapered mating portions.

The invention features an electrode assembly for use in a biomedical electrode unit having a pad with a hole in it for receiving the electrode assembly. The improvement includes a first member disposed on one side of the pad and having a stud portion which extends axially through the hole in the pad, and contains on it a first mating area. There is a second member disposed on the other side of the pad and having an aperture in it containing a second mating area which snugly engages the first mating area of the stud portion. A connector member extends axially through the hole in the pad and into the first and second members for securely connecting together the first and second members with the pad between them and the connector member may be integral with either of the other members.

In preferred embodiments, the stud portion and the aperture are mutually tapered at least where they engage with each other at the mating surfaces. The first member may be a cap which receives an electrical contact or lead from monitoring equipment, and the second member may be a base which is connected to the skin, either directly or through a gel-soaked disc of sponge rubber or like. Each of the first and second members including the mating areas may be electrically conductive, or at least functional portions of the surfaces of each of those first and second members and their mating areas may be electrically conductive. The first member and the connector member may be electrically conductive or may have at least portions of their surfaces electrically conductive, with the connector member extending from the first member through the second member to make contact with the skin directly or through a gel-soaked disc.

DISCLOSURE OF PREFERRED EMBODIMENTS

Other objects, features and advantages will occur from the following description of a preferred embodiment and the accompanying drawings, in which.

The invention may be accomplished with an electrode assembly used in a biomedical electrode unit which has a contact pad with a hole in it for receiving the electrode assembly. There is a first member on one side of the pad which has a stud portion which extends axially through the hole in the pad. The stud portion carries a first mating area. A second member is disposed on the other side of the pad and has an aperture with a second mating area, which snugly engages the first mating area of the stud portion.

The connector member extends axially through the hole in the pad and into the first and second members for securely connecting together the first and second members and may be integral with either of them.

Typically, each of the first and second members, including their respective mating areas, are electrically conductive, for example where the parts are all made of metal. If the parts are made of plastic with metallized conductive coating, then at least functional portions of the surfaces of each of the first and second members, including the mating areas, is electrically conductive to maintain electrical continuity through the electrode assembly.

The first member and the connector member may be electrically conductive or have portions of their surface made electrically conductive, such as by metal plating, so that the connector member extends through the first member, which may be for example the cap, through the second member, which may be for example the base, to contact the skin or at least the gel-soaked disc which contacts the skin.

The stud portion and the aperture on the respective first and second members may be mutually tapered, at least where they engage with each other at the mating surfaces. This tapering insures good, solid electrical contact between the mating surfaces where the tapers have wedged together. It also provides a self-stabilizing fitting between the two members so that they do not tend to tilt or wobble with respect to each other. Also, because of the wedging action of the tapered, interfitting mating surfaces, the spacing between the two members is fixed so that they maintain a predetermined gripping action with the intermediate pad.

Figure 1:
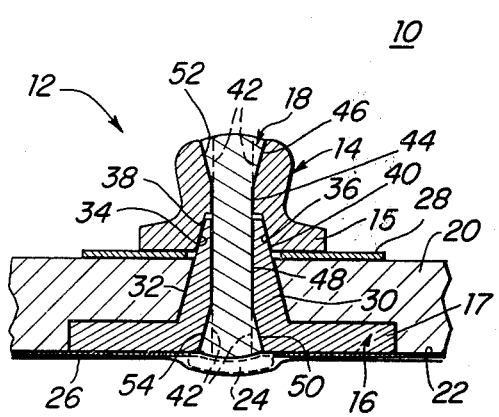
FIG. 1 is a schematic sectional view with portions removed of a biomedical unit using an electrode assembly according to this invention.
Figure 2:
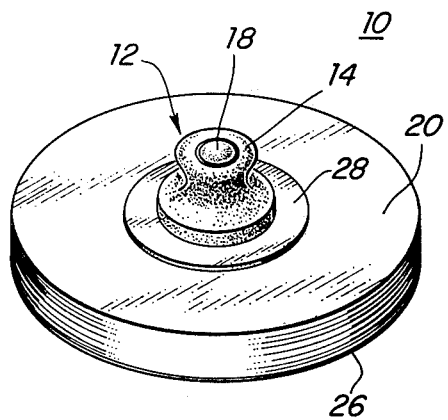
FIG. 2 is a more complete axonometric view on a reduced scale of the biomedical electrode unit using the electrode assembly of FIG. 1.

There is shown in FIGS. 1 and 2 a biomedical electrode unit 10 including an electrode assembly 12, including an upper member or cap 14 with flange 15, lower member or base 16 with flange 17, and connector member or pin 18. Held in position between cap 14 and base 16 is an adhering pad 20 which carries along its bottom surface and the bottom surface of base 16 an adhesive layer 22 for adhering to the skin of the user. A sponge-like disc 24 impregnated with a conductive gel may be placed beneath the center of the electrode and a removable paper sheet 26 may be used to protect the adhesive and the gel before use. Typically, an enlarged washer 28 is employed between cap 14 and pad 20 to provide a greater area of gripping so that washer 28 and base 16 have approximately the same diameter, with base 16 being typically slightly larger.

Base 16 includes an axially upstanding stud 30, which may be tapered 32 throughout its extent, but at a minimum is tapered at the mating surface 34 where stud 30 engages with a similar tapered mating surface 36 in aperture 38 of cap 14. The aperture 38 may also be generally tapered as at 40. Pin 18 may take various forms and may be secured to base 16 and cap 14 in various ways. In FIGS. 1 and 2, pin 18 may originally have a wholly cylindrical shape as indicated by the phantom lines 42 at its upper and lower ends. Then cap 14 has a cylindrical bore 44 with a flare mouth 46; and base 16 has a similar cylindrical bore 48 with a flared mouth 50. For assembly then, pin 18 is mounted in and may be integral with cap 14 and base 16 and its ends are spread to the presently shown flared shape 52 at the upper end and 54 at the lower end, so that pin 18 is spread to fill the flared mouth 46 and 50, respectively. Alternatively, pin 18 may be installed in either the cap 14 or base 16 first, then inserted through pad 20 and washer 28, following which the flaring of the other end of pin 18 is effected in the remaining unattached one of cap 14 and base 16. The tapered area, especially at mating surfaces 34 and 36, insures a tight fit between cap 14 and base 16 which prevents wobbling of cap 14 and base 16 with respect to each other and positively limits the spacing between them in order to properly secure pad 20. In addition, when cap 14 and base 16 are made of electrically conductive material, electrical continuity is assured from an electrical connection which grips cap 14 through the positive gripping of the wedged-together surfaces 34 and 36 and then though base 16, either directly or through the gel-soaked disc 24. If pin 18 is also a conductive material, this too acts as a conductive path from cap 14 to base 16 and gel-soaked disc 24.

Figure 3:
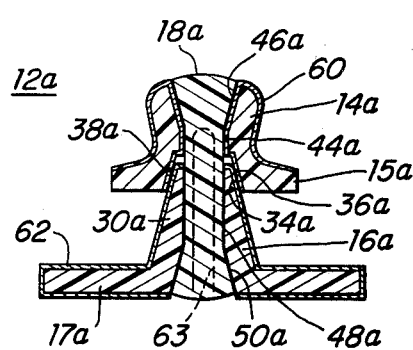
FIG. 3 is a schematic sectional view of an alternative embodiment of the electrode assembly shown in FIG. 1.

Although in FIGS. 1 and 2 caps 14 and 16 have been indicated as being made of electrically conductive material such as metal and pin 18 may or may not be of such a material, this is not a necessary limitation. For example, as shown in FIG. 3, where as in subsequent figures like parts have been given like numbers and similar parts like numbers accompanied by a successive lower case letter, cap 14a and base 16a are formed of a non-electrically conductive material. Therein cap 14a includes on at least the necessary functional portions of its surface a conductive layer 60 for connection with a lead for monitoring equipment, which conductive surface at mating area 36a connects with a similar conducting surface 62 on base 16a at mating surface 34a.

Pin 18a may be made of conductive or non-conductive material and if it is conductive material or non-conductive material with a conductive surface and there are suitable conducting surfaces interfacing with it on cap 14a and 16a, then it too acts as a conductive path in addition to the positive primary path through the mating surfaces 34a and 36a. Pin 18a may be hollow for at least a portion of its length to reduce weight and cost, as indicated in phantom at 63.

Figure 4:
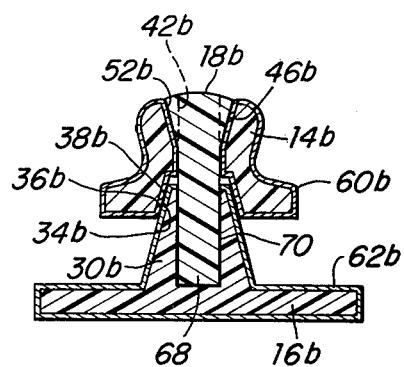
FIG. 4 is a schematic sectional view of an alternative construction of an electrode assembly with the connector member mounted in the base member.

Alternatively, pin 18b, FIG. 4, may be attached at one end 68 to base 16b such as by mounting in bore 70 while maintaining its previously explained flared form 52b derived from the original cylindrical form 42b for mating with the flared mouth 46b of cap 14b.

Figure 5:
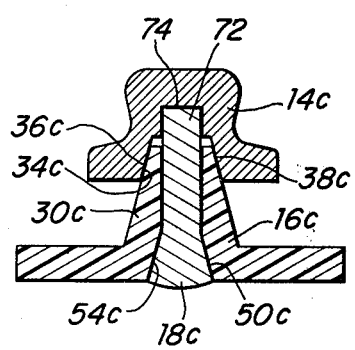
FIG. 5 is a view similar to FIG. 4 with the connector member mounted in the cap member.

Conversely, pin 18c, FIG. 5, may have end 72 fitted in bore 74 of cap 14c and may be integral therewith, with its lower end flared 54c to grip flared mouth 50c of base 16c.

Figure 6:
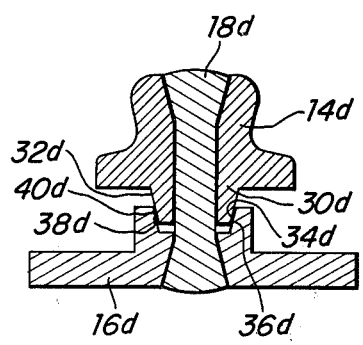
FIG. 6 is a schematic sectional view of an electrode assembly with the tapered surfaces reversed with respect to those shown in FIG. 1.

Although thus far in each of the illustrations it is cap 14 which contains a tapered aperture 38 and base 16 which contains a tapered stud 30, this is not a necessary limitation of the invention, for as shown in FIG. 6, cap 14d may include a stud portion 30d having a general taper 32d with a mating surface 34d that engages with mating surface 36d of general taper 40d of aperture 38d located on base 16d. Cap 14d and base 16d are held together in the usual fashion by pin 18d.

Other embodiments will occur to those skilled in the art and are within the following claims:

What is claimed is:

1. In an electrode unit having an electrode assembly and a contact pad with an opening in it for receiving the electrode assembly, an improved electrode assembly comprising: a first member disposed on one side of said pad with a stud portion extending axially through the opening in the pad, a first mating area on the study portion and a first hole therein; a second member disposed on the other side of the pad and having an aperture with a second mating area engaging with said first mating area of said stud portion and a second hole therein; a connector member extending axially through the opening in the pad and into the first and second holes and securing together said first and second members with pad between them; and conductive means extending through said members to provide a continuous electrical path through the electrode assembly.

2. The electrode assembly of claim 1 in which said stud portion and said aperture are mutually tapered where they engage with each other at the mating surfaces.

3. The electrode assembly of claim 1 in which said first member is a cap for receiving an electrical contact and said second member is a base which is adapted for connection to the skin.

4. The electrode assembly of claim 1 in which each of said first and second members including said mating areas are electrically conductive.

5. The electrode assembly of claim 1 in which at least portions of the surface of each of said first and second members including said mating areas are electrically conductive.

6. The electrode assembly of claim 1 in which said first member and said connector member are electrically conductive and said connector member extends through said second member.

7. The electrode assembly of claim 1 in which at least a portion of the surfaces of said first member and said connector member are electrically conductive and said connector member extends through said second member.

* * * * *